US009138257B2

(12) United States Patent
Revivo

(10) Patent No.: US 9,138,257 B2
(45) Date of Patent: Sep. 22, 2015

(54) ROTATING HANDHELD MOTORIZED HAND-PIECE INCLUDING COMBINATION INTERCHANGEABLE MICRODERMABRASION BRUSH HEAD, INTERCHANGEABLE HEADS HAVING A LATEX SPONGE, AND HOOK AND LOOP FASTENERS TO REMOVABLY RETAIN CLEANING PADS

(71) Applicant: Jacob Revivo, Sun Valley, CA (US)

(72) Inventor: Jacob Revivo, Sun Valley, CA (US)

(73) Assignee: Spa De Soleil, Inc., Sun Valley, CA (US)

( * ) Notice: Subject to any disclaimer, the term of this patent is extended or adjusted under 35 U.S.C. 154(b) by 0 days.

(21) Appl. No.: 13/888,100

(22) Filed: May 6, 2013

(65) Prior Publication Data

US 2014/0330289 A1    Nov. 6, 2014

(51) Int. Cl.
*A61B 17/50* (2006.01)
*A61B 17/54* (2006.01)
*A45D 34/04* (2006.01)
*A61H 7/00* (2006.01)
*A61B 17/32* (2006.01)
*A61B 17/00* (2006.01)

(52) U.S. Cl.
CPC ............... *A61B 17/54* (2013.01); *A45D 34/04* (2013.01); *A45D 34/042* (2013.01); *A61H 7/005* (2013.01); *A45D 2200/1018* (2013.01); *A45D 2200/1054* (2013.01); *A61B 2017/00398* (2013.01); *A61B 2017/00473* (2013.01); *A61B 2017/00477* (2013.01); *A61B 2017/00734* (2013.01); *A61B 2017/320004* (2013.01); *A61B 2017/320012* (2013.01)

(58) Field of Classification Search
CPC ............. A61B 17/54; A61B 2017/320004; A61B 2017/00761; A61B 13/02; A61C 17/26; A61C 17/3436; A47L 11/4063; A45D 29/05; A45D 29/14; A45D 29/18
USPC ........ 15/22.1, 28, 97.1–97.2, 230.17, 230.19; 132/73.6, 75.8, 76.5; 451/344, 357, 451/359, 490, 523–525, 538; 601/17, 601/84–85, 87, 89, 92–94, 112, 114, 134, 601/136–138; 606/131–134, 171, 178–180
See application file for complete search history.

(56) References Cited

U.S. PATENT DOCUMENTS

| | | | |
|---|---|---|---|
| 4,131,966 A * | 1/1979 | Gross | 15/28 |
| 5,187,827 A * | 2/1993 | Wei | 15/22.1 |
| 5,471,695 A | 12/1995 | Aiyar | |
| 6,253,405 B1 * | 7/2001 | Gutelius et al. | 15/22.2 |
| 6,401,289 B1 | 6/2002 | Herbert | |
| 6,629,983 B1 | 10/2003 | Ignon | |
| 6,981,953 B1 | 1/2006 | Ko | |

(Continued)

*Primary Examiner* — David Eastwood
(74) *Attorney, Agent, or Firm* — Thomas I. Rozsa

(57) ABSTRACT

A handheld apparatus including (a) a motorized hand-piece including a mechanical rotatable coupling shaft which is caused to rotate so that it imparts a rotating motion to the coupling shaft; (b) an interface cup member which includes a body with an exterior surface having hook and loop fasteners thereon and a lower surface with an interface opening which is affixed to the coupling member of the mechanical rotatable shaft; and (c) the hand-piece individually retaining a multiplicity of different interchangeable components which are used for different purposes, each different component affixed on one surface to the hook and loop fasteners of the interface cup and which rotate when the motorized hand piece is energized and causes the interface cup to rotate.

9 Claims, 13 Drawing Sheets

(56) References Cited

U.S. PATENT DOCUMENTS

| | | |
|---|---|---|
| 7,179,152 B1 * | 2/2007 | Rhoades .................. 451/41 |
| 7,367,981 B2 | 5/2008 | Bernaz |
| 7,384,405 B2 | 6/2008 | Rhoades |
| 7,572,238 B2 | 8/2009 | Rhoades |
| 8,157,465 B2 | 4/2012 | Duru |
| 2003/0125754 A1 * | 7/2003 | Davis et al. ............... 606/133 |
| 2006/0058714 A1 * | 3/2006 | Rhoades .................. 601/73 |
| 2007/0066919 A1 | 3/2007 | Gueret |
| 2010/0120342 A1 * | 5/2010 | Rivard et al. ............... 451/359 |
| 2010/0217263 A1 * | 8/2010 | Tukulj-Popovic ........... 606/43 |
| 2011/0270274 A1 * | 11/2011 | Hull, Jr. .................. 606/131 |
| 2012/0233798 A1 | 9/2012 | Brewer et al. |
| 2013/0023806 A1 * | 1/2013 | Ungemach et al. .......... 601/114 |

* cited by examiner

ROTATING HANDHELD MOTORIZED HAND-PIECE INCLUDING COMBINATION INTERCHANGEABLE MICRODERMABRASION BRUSH HEAD, INTERCHANGEABLE HEADS HAVING A LATEX SPONGE, AND HOOK AND LOOP FASTENERS TO REMOVABLY RETAIN CLEANING PADS

BACKGROUND OF THE INVENTION

1. Field of the Invention

The present invention relates to the field of cosmetic cleaning machines which are used to gently perform dermabrasion on facial skin, apply makeup and clean pores in the skin.

2. Description of the Prior Art

The following 11 prior art patent and published patent applications are the closest prior art to the present invention:

1. U.S. Pat. No. 5,471,695 issued to Sanjay Aiyar on Dec. 5, 1995 for "Motorized Brush" (hereafter the "Aiyar Patent");

2. U.S. Pat. No. 6,401,289 issued to Linda S. Herbert on Jun. 11, 2002 for "Skin Cleaning Device" (hereafter the "Herbert Patent");

3. U.S. Pat. No. 6,629,983 issued to Roger G. Ignon on Oct. 7, 2003 for "Apparatus and Method for Skin/Surface Abrasion" (hereafter the "Ignon Patent");

4. U.S. Pat. No. 6,981,953 issued to Fu-Chung Ko on Jan. 3, 2006 for "Dual-Functional Massage Bar Used In Bath" (hereafter the "Ko Patent");

5. United States Published Patent Application No. 2007/0066919 to Jean-Louis Gueret on Mar. 22, 2007 for "Massage Device And Method" (hereafter the "Gueret Published Patent Application");

6. U.S. Pat. No. 7,367,981 issued to Gabriel Bernaz on May 6, 2008 for "Device for Dermabrasion" (hereafter the "Bernaz Patent");

7. U.S. Pat. No. 7,384,405 issued to Dean L. Rhoades on Jun. 10, 2008 for "Oxygenating Cosmetic Instrument Having Various Numbers of Heads" (hereafter the "'405 Rhoades Patent");

8. U.S. Pat. No. 7,572,238 issued to Dean L. Rhoades on Aug. 11, 2009 for "Handheld Sonic Microdermabrasion Porous Applicator" (hereafter the "'238 Rhoades Patent");

9. United States Published Patent Application No. 2011/0270274 to Raymond J. Hull, Jr. on Nov. 3, 2011 for "Handheld, Personal Skin Care Systems With Detachable Skin Care Elements" (hereafter the "Hull Published Patent Application");

10. U.S. Pat. No. 8,157,465 issued to Nicolas Duru Apr. 17, 2012 for "Applicator and a Kit Including Such An Applicator" (hereafter the "Duru Patent");

11. United States Published Patent Application No. 2012/0233798 to Gerald K. Brewer et al. and assigned to Pacific Bioscience Laboratories, Inc. on Sep. 20, 2012 for "Brushhead For Electric Skin Brush Appliance" (hereafter the "Brewer Published Patent Application").

The Aiyar Patent discloses a motorized brush which imparts vibrational motion to a scrubbing brush head. The brush includes a water-tight housing, in which a small electric motor is mounted. The motor includes an eccentric weight mounted to its drive shaft. In use, the motor is energized, causing the eccentric weight to be rotated. The eccentric weight vibrates the brush head without rotating it. This vibrational motion provides an effective scrubbing action without the necessity for complex sealing mechanisms connecting the brush head to the motor shaft.

The Herbert Patent discloses a skin cleaning device for removing dirt, oils and dead skin. The skin cleaning device includes a housing having a first end and a second end. The first end has a cavity extending therein. A motor is positioned in the housing and is located generally adjacent to the second end. A shaft is mechanically coupled to the motor and extends through the second end of the housing. The motor is adapted for rotating the shaft. The shaft has a free end defining a female coupler. A power supply is operationally coupled to the motor. A disc has a first side and a second side. The first side has a convex shape. A male coupler is integrally attached to the second side and is generally centrally located on the second side of the disc. The male coupler is removably insertable into the female coupler for releasably attaching the disc to the shaft. A plurality of cleaning pads each has a peripheral edge. An elastic member is attached to and extends around the peripheral edge such that each of the pads forms a sock positionable over the first side of the disc. The motor rotates the disc such that the pads may be used for cleaning skin of the user.

The Ignon Patent discloses a dermabrasion hand-piece adapted for use to abrade the skin of a patient which includes a housing extending along an axis between a proximal end and a distal end. Portions of the housing define a hole at the distal end with an abrasion element disposed in the housing in proximity to the hole. The housing is adapted for connection to a vacuum source to pull a portion of the skin through the hole and to move the skin portion into contact with the abrasion element. Movement of the abrader relative to the skin abrades tissue from the skin portion extending through the hole. The abrader can be provided in the form of a roller or blade moveable relative to the housing to abrade the skin. The abrasion element can be selected from a series of elements each having different abrasion characteristics and can be mounted in either the cap or the base of the housing.

The attachment mechanisms are retained by suction.

The Ko Patent discloses a dual-functional massage bar used in a bath which includes a main body which is combined by a pair of corresponding halves having a plurality of balls disposed spaced apart on one side, a piece of first Velcro® attached to the other side opposite to the balls for engaging a piece of sponge which has a piece of second Velcro on its underside engaged with the piece of the first Velcro®, an externally threaded tubular adapter on the rear end of the main body in which is a motor and a vibrator, a tube having internal threads screwed onto the tubular adapter with a pair sealing rings engaged therein between, a pair of batteries disposed into the tube and the adapter and biased by a spring and three switch buttons spacedly disposed on the front side of the main body and protected by a piece of thin membrane. The piece of sponge may be replaced by a brush and/or a piece of cloth.

The Gueret Published Patent Application deals with a massage member and Paragraphs 0055 through 0062 state the following:

"The membrane 4 may be secured in various ways to the handle 2, and the frame 3 may be overmolded onto the membrane, for example, or vice versa. In exemplary embodiments, the membrane 4 may be secured to the frame 3 by heat-sealing or by adhesive, or may be held thereon by a holding part, as described below.

It is also possible for the massage member 4 to be mounted removably, thereby making it possible, for example, for the user to clean the massage member 4 more easily, or to select the massage member 4 as a function of the treatment to be performed.

As illustrated in FIG. 5, the massage member 4 may be configured in such a manner as to be fastened in an interchangeable manner on the handle 2, by snap-fastening on the frame 3, for example. At the periphery, the massage member 4 may include a bead 9 that may be configured to snap-fasten in an annular groove 10 formed on an inside surface of the frame 3.

By including a massage member 4 that may be removably-fastenable, the user may use a single handle 2 and a plurality of massage members 4 including different characteristics, the user being able to select the massage member 4 that may be suitable for a particular region of the body or of the face, and/or that may be suitable for a type of treatment to be performed, for example, stimulating blood circulation, lymphatic drainage, dermabrasion, or applying a composition.

For example, the massage members 4 associated with the handle 2 may include portions in relief 7 that are different.

FIG. 7 illustrates the possibility of the handle 2 including a removable frame 3. The massage member 4 may then be capable of being connected in a non-removable manner to the frame 3.

The user may thus replace a frame 3 provided with a massage member 4 with another frame 3 provided with a different massage member.

For example, the frame 3 may be fastened in a removable manner on the body 11 of the handle by co-operating portions in relief 12 and 13."

The Bernaz Patent discloses the concept of having removable abrasive pieces as disclosed in Column 2 Lines 49 through 58 which read as follows: Advantageously, the abrasive surface is carried on a removable piece of rigid or flexible material on the oscillating support. Thus, the device can include several interchangeable pieces each with a different abrasive surface and/or of a different size. For example, one can have several interchangeable pieces having an identical abrasive surface, but with different lengths adapted to skin treatment on different parts of the body, and/or several interchangeable pieces with different abrasive surfaces designed to produce a more or less pronounced microabrasion."

The '405 Rhoades Patent discloses an apparatus including a handle capable of manipulation by a human hand, and one or more head portions to mate to various types of treatment attachments, which may be moved over an area of skin and/or body part by a motion generator moving the head portions, and/or by a user manipulating the handle. Various suitable attachments include applicator attachments having abrasive surfaces, oxygenating attachments having pores through which oxygen may travel, brush attachments for cleaning and polishing, thermal attachments for heating and cooling, and light radiating attachments. The motion generator may move the attachments by vibrating, spinning, oscillating, or propagating sonic waves through the head portions. Thus, attachments may be attached and removed from the head portions to treating skin and/or body parts by abrasion, cleaning, polishing, lighting, or oxygenation. Moreover, during treatment abrasive composition, cleaning solution, and/or polishing solution may be applied to the skin and/or body part.

The '238 Rhoades Patent again is a handheld sonic microdermabrasion porous applicator. It discloses a composition including a base and a plurality of abrasive particles. An apparatus including a head, and an applicator coupled to the head, the applicator having dimensions suitable for contacting localized areas of human skin. A method including applying a composition to an area of human skin, the composition comprising a base and a plurality of abrasive particles, and manipulating the composition over the area of human skin with a handle-operated instrument.

The Hull Published Patent Application discloses in Paragraphs 28 through 31 the following:

"Referring again to FIG. 1, the skin care element holder 200 is a substantially circular plate 202 having a diameter between about 20 mm and about 60 mm. It has a first surface 204 arranged and configured for coupling to the skin care element 100, a second surface 206, opposite the first surface, and an outer peripheral edge 208. The second surface is shown in more detail in FIG. 3. The second surface 206 has a plurality of engagement arms 210 extending from the second surface 206 in a direction away from the first surface, at least one of said engagement arms comprising a snap-fit projection 212 for engagement with recesses in an associated receptacle. At least one spacer leg 214 extends from the second surface 206 in a direction away from the first surface 204 to support the plate 202 when fitted into an associated receptacle. This spacer leg 214 also adds strength to the skin care element holder 200 to help resist damage, especially when the system is mishandled and/or dropped. The plate 202 also has at least one key 216 extending from the second surface 204 in a direction away from the first surface that is arranged and configured to fit into a notch in an associated receptacle. The second surface 206 may also have one or more optional centering flange(s) 218 to improve the fit of the skin care element holder 200 in the receptacle 12. Like the spacer leg(s), this centering flange 218 also adds strength to the skin care element holder 200 to help resist damage. Alternatively, the functions of the spacer leg(s) and the centering flange(s) may be combined into one or more separate structures spaced about the second surface 206.

The engagement arms 210 provide a snap-fit engagement with recesses in an associated receptacle to hold the plate 202 in place during use. Preferably, there are three engagement arms 210, each having a snap-fit projection 212 extending outwardly from the center of the substantially circular plate 202. Alternatively, one or two of the three engagement arms 210 have a flange to fit into a recess associated with a mating receptacle, and the remaining engagement arm(s) have a snap-fit projection. Thus, much like a battery compartment door, one or more flanges fit into a recess in a receptacle, and an opposite engagement arm has a snap fit project to secure the plate in place for use. Preferably, the three engagement arms 210 are substantially evenly spaced around the substantially circular plate 202, such as about 120.degree. around the plate 202. In addition, the engagement arms 210 are disposed proximate, but spaced inward from the outer peripheral edge 208. This permits the second surface 206 of the plate 202 to be positioned above a rim of a receptacle of a handheld body.

Preferably, the at least one spacer leg 214 engages with a surface in an associated receptacle to support the therein. This reduces the likelihood of significant relative motion between the plate 202 and the associated receptacle that may cause an audibly perceptive rattle during use. In addition, the at least one key 216 extending from the second surface 204 of the plate 202 can engage a notch in an associated receptacle. This key 216 can cooperate with the engagement arms 210 to prevent significant relative rotational motion between the plate 202 and receptacle 12 during use.

Preferably, the outer peripheral edge 208 of the substantially circular plate 202 is the outer circumference of a circle of constant radius from the center of the plate. In this embodiment, the plate 202 is truly circular. Alternatively, the outer peripheral edge 208 is defined by a geometrical surface having a variable radius from the center of the plate; however, the maximum radius and minimum radius have a difference of less than about 3 mm, and more preferably of less than about 2 mm. This generally circular form of the plate improves the safety of the system for a rotating or oscillating skin care system. In yet another alternative form, the outer peripheral edge 208 may have a resilient material 220 (as shown in FIG. 3B) disposed thereon to cushion any irregularities in the peripheral edge 208."

The Duru Patent discloses: an applicator for applying a composition to the human body, the applicator comprising: a support that is configured to be mounted in removable manner on an appliance that enables movement to be transmitted to said support; a reservoir that is secured to the support and that contains the composition, the reservoir being defined, at least in part, by at least one closure element; an applicator element that is secured to the support at least during use; and an opener element that is suitable for acting on the closure element in order to put the reservoir and the applicator element into communication.

The Brewer Published Patent Application discloses the brushhead which is used in a power skin brush appliance which includes a drive system having a single drive member. The brushhead includes a base assembly mountable to the drive system with an optional outer annular fixed portion and an inner portion which in operation oscillates back and forth at a selected sonic frequency through a selected angle in response to action of the drive system. Mounted on the outer portion is a first group of filament tufts. Mounted on the oscillating portion are three concentric groups of filament tufts. Each oscillating group of filament tufts includes two annular rings of filament tufts. The filament tufts in the oscillating filament tuft groups have a selected physical characteristic which in one embodiment is diameter, which differs between the respective oscillating filament tuft groups sufficiently to produce a differential stiffness between the filaments thereof to in turn produce an out of phase motion of the tips of the filaments between the three oscillating filament tuft groups.

SUMMARY OF THE INVENTION

The present invention is a rotating handheld motorized hand-piece having a mechanical rotatable coupling shaft with a coupling member at its distal end onto which interchangeable cleaning and exfoliating members are retained, which includes the combination of a retaining cup having a retaining cup opening removably affixed onto the rotatable coupling shaft of the motorized hand-piece. On its opposite side the retaining cup has a removable mating means such as hook or loop fastener. The interchangeable components are affixed to a base which has a mating hook and loop fastener on a first surface of the base and the exfoliating member affixed to the opposite side of the base. Therefore, the present invention is a device which enables interchangeable components to be removably affixed to the motorized hand-piece. The interchangeable components include a base with a mating hook or loop fastener on one side and a microdermabrasion brush on the other side, or the base having mating hook and loop fastener on one side and a latex sponge for moisturizing cream and makeup application retained on the other side, or the base having mating hook and loop fastener on one side and another hook or loop fastener on the other side to removably retain a deep cleaning pad. The pad has a Velcro® attachment so that the pads can be used for as long as they are usable and then discarded and only the pads need to be replaced and not the entire brush assembly.

Therefore, the key features are the combination of a interfacing cup which is coupled to the coupling member on the hand-piece and has a hook and loop fastener which can removably retain a base selected from the group consisting of: a base having a mating hook and loop fastener on one side of the base and an exfoliating brush on the other side of the base, a mating hook and loop fastener on one side of the base and a latex sponge to apply moisturizing cream and makeup on the other side of the base, and a mating hook and loop fastener on one side of the abase base and a hook and loop attachment to removably retain deep cleansing pads embedded on the other side of the base.

It is therefore an object of the present invention to provide a motorized hand-piece and a mechanically rotatable coupling shaft onto which a removable coupling member or permanently affixed coupling member is coupled on one side and a retaining means to removably retain a base with a mating hook and loop fastener on one side and a facial cleansing apparatus on the other side which is comprised of the group selected from a microdermabrasion exfoliating brush which rotates to remove an upper layer of dead skin when a motor to which the rotatable coupling shaft is connected by a gear assembly is energized, a latex sponge for moisturizing cream and makeup application retained in a sponge retaining cup coupled to a coupling member on the rotatable shaft so that the latex sponge rotates to apply moisturizing cream and to also apply makeup when a motor to which the rotatable coupling shaft is connected by a gear assembly is energized, and an interchangeable cleaning and exfoliating members is retained, which includes a hook and loop fastening member retained within a retaining member and which removably retains a deep cleansing pad for cleansing the skin, the deep cleansing pad removable and replaceable with a new pad so that only the deep cleansing pad needs to be replaced instead of the entire hook and loop assembly.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
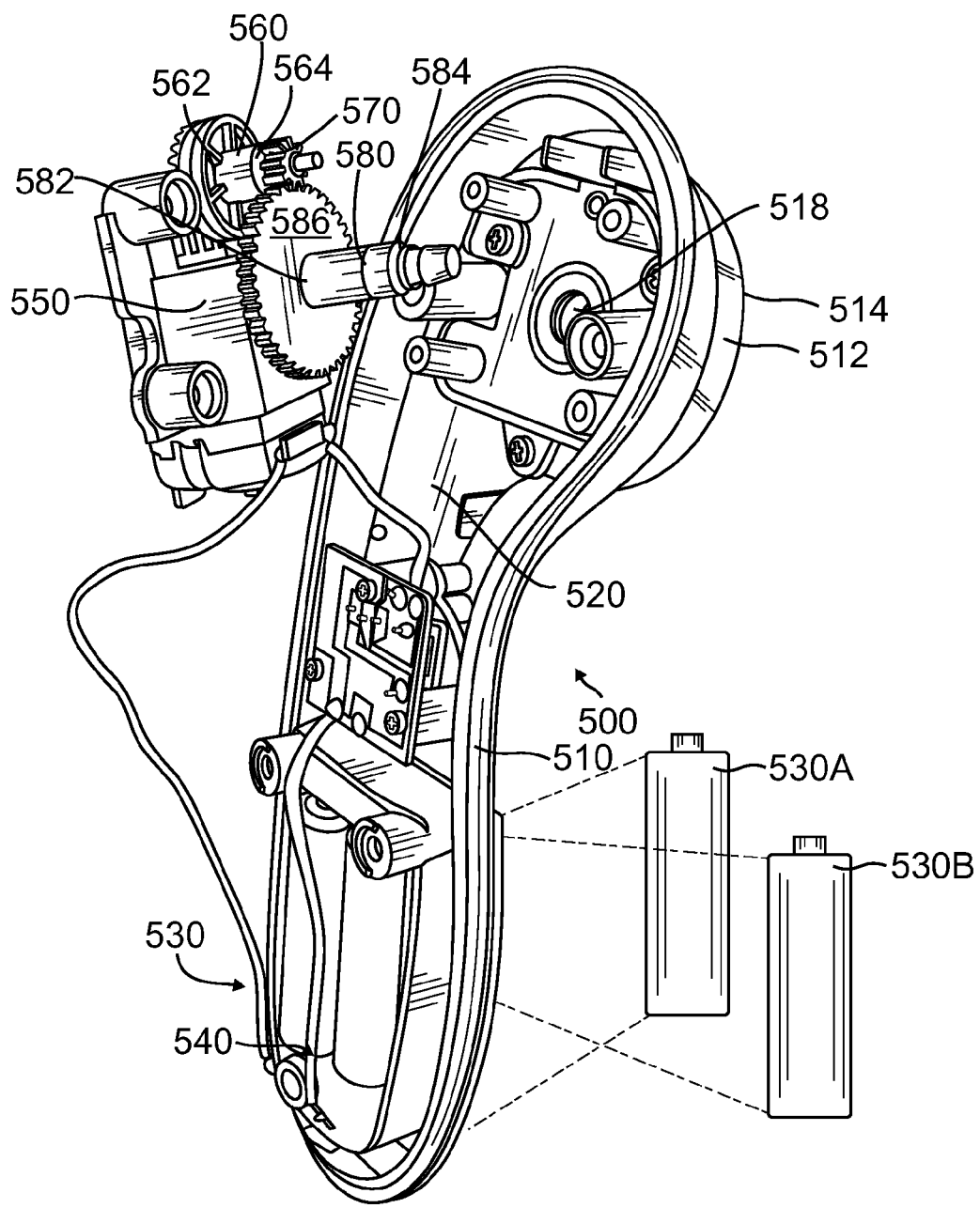
FIG. 1 is an exploded view of the motorized hand-piece with a mechanical rotatable coupling shaft used with the present invention.

FIG. 1 is an exploded view of a motorized hand-piece used with the present invention. The basic components of the hand-piece 500 include an outer shell 510 which surrounds an interior chamber 520. The interior chamber includes a power source member 530 which, by way of example, is a multiplicity of batteries 530A, and 530B, which preferably are AA batteries. While two batteries are illustrated, some power source members have more than two batteries. An access door (not shown) in outer shell 510 facilitates access to the battery chamber 530 which retains the batteries. In one variation, a plug member 540 is used to connect the hand-piece 500 to a source of external power such as 120V electricity outlet. Some hand-pieces contain transformers used to reduce the voltage to 12 volts DC from a 120-volt AC source.

The power source member 530 is electrically connected to a motor 550 which is usually a DC motor which in turn is connected to a shaft 560 with at least one gear 570 at the distal end 564 of the shaft remote from the proximal end 562 of the shaft connected to the motor 550. The hand-piece exterior shell 510 can be any desired shape to facilitate the hand-piece being held in one hand. The hand-piece 500 usually includes a raised section 512 having a flat upper surface base 514 surrounding an opening 518 through which a mechanical rotatable coupling shaft 580 extends through its distal end 584. At its proximal end 582 within chamber 520, the proximal end 582 of the mechanical rotatable coupling shaft 580 has at least one gear 586 which is intermeshed with the at least one gear 570 of the motor 550 so that as gear 570 rotates when the motor 550 is energized, the mechanical rotatable coupling shaft 580 is caused to rotate so that it imparts a rotating motion which is parallel to the upper surface 514 of hand-piece 500 to an object affixed to a coupling member 588 at the distal end 584 of the mechanical rotatable coupling shaft 580. The hand-piece 500 also includes an on/off switch 590 (see FIG. 2).

When depressed, the on/off switch 590 closes an electric circuit connecting the motor 550 to the source of power 530 and the intermesh movement of the respective at least one gears 570 and 586 causes rotational motion of the mechanical rotatable coupling shaft 580. The rotational motion of the mechanical rotatable coupling shaft 580 can be clockwise or counter-clockwise. The on-off switch 590 can also have a programmed chip or other mechanism which causes the mechanical rotatable coupling shaft 580 to rotate clockwise when depressed once, rotate counter-clockwise if depressed a second time, and open the electrical connection between the motor 550 and source of power 530 and turn the motor 550 off when depressed an additional time. Therefore, the options are to have the mechanical rotatable coupling shaft 580 rotate in both the clockwise and counter-clockwise direction or to rotate in only one of the directions.

The hand-piece 550 has been described in detail to illustrate one hand-piece to be used with the present invention. Any other hand-piece is also within the spirit and scope of the present invention. The key requirements are a rotating coupling shaft to which an object is connected, a source of power, a motor and a switch which turns the motor on and off and when the motor is on, the rotatable coupling shaft rotates in either a clockwise or counter-clockwise direction.

Figure 2:
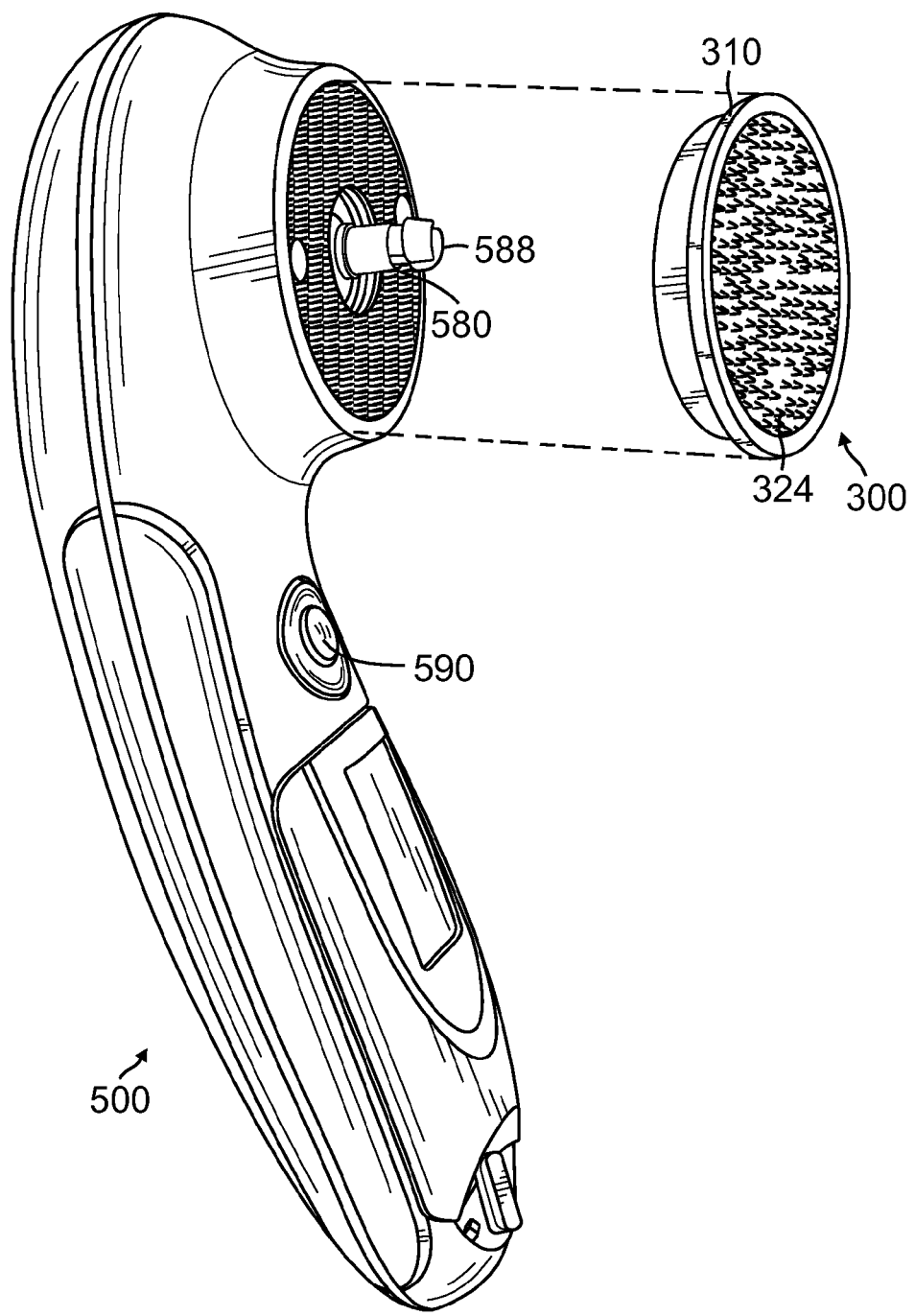
FIG. 2 is an exploded side perspective view of the motorized handheld piece and a mechanical rotatable coupling shaft onto which the interface cup member is inserted with the interface cup member shown on the right side illustrating in a front perspective view illustrating the hook and loop fastener members on the upper surface of the interface cup member.
Figure 2A:
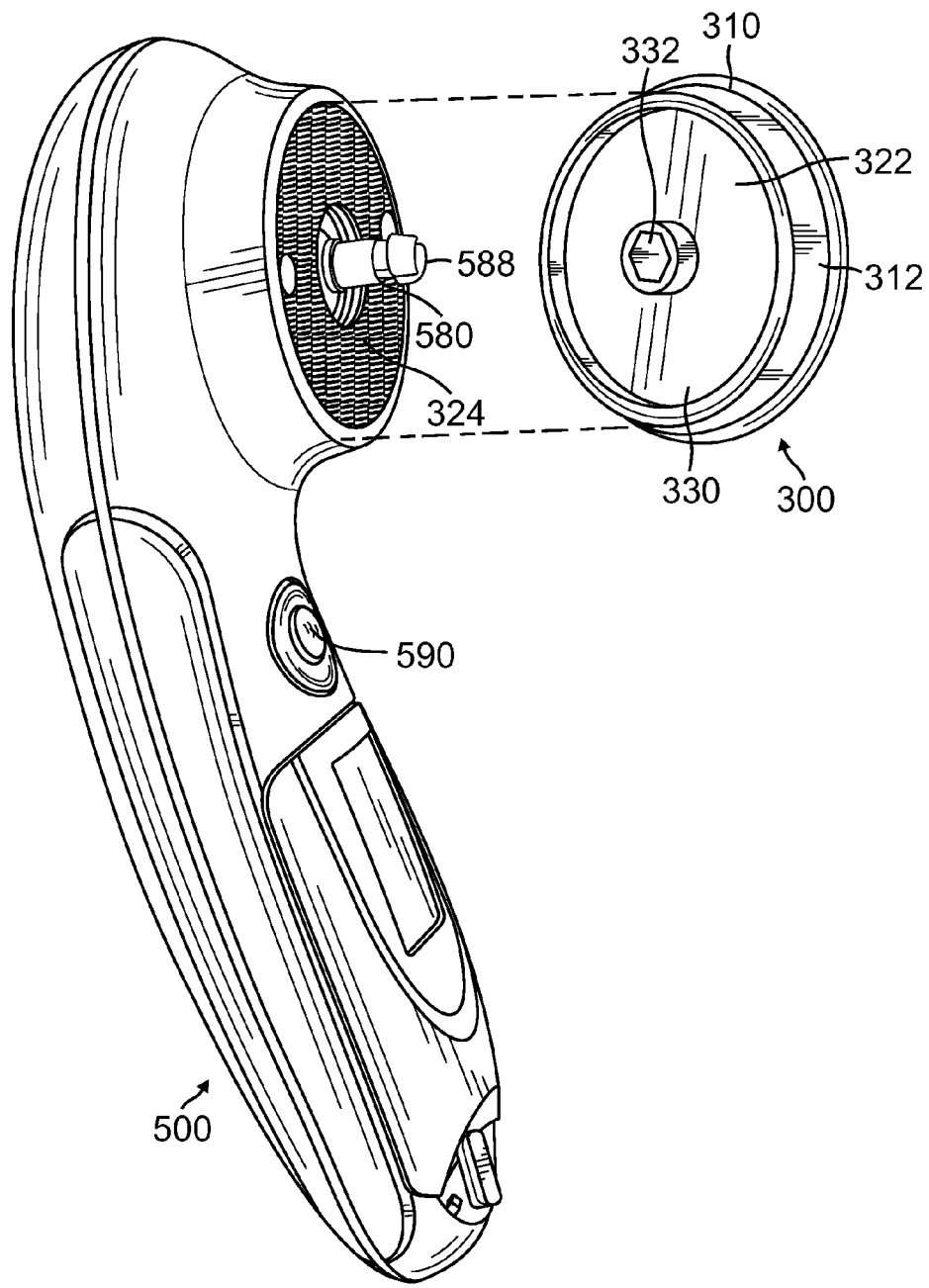
FIG. 2A is an exploded side perspective view of the motorized handheld piece and a mechanical rotatable coupling shaft onto which the interface cup member is inserted with the interface cup member shown on the right side illustrating a rear perspective view of the interface cup member showing the attaching mechanism which will be affixed to the mechanical rotatable coupling shaft.
Figure 2B:
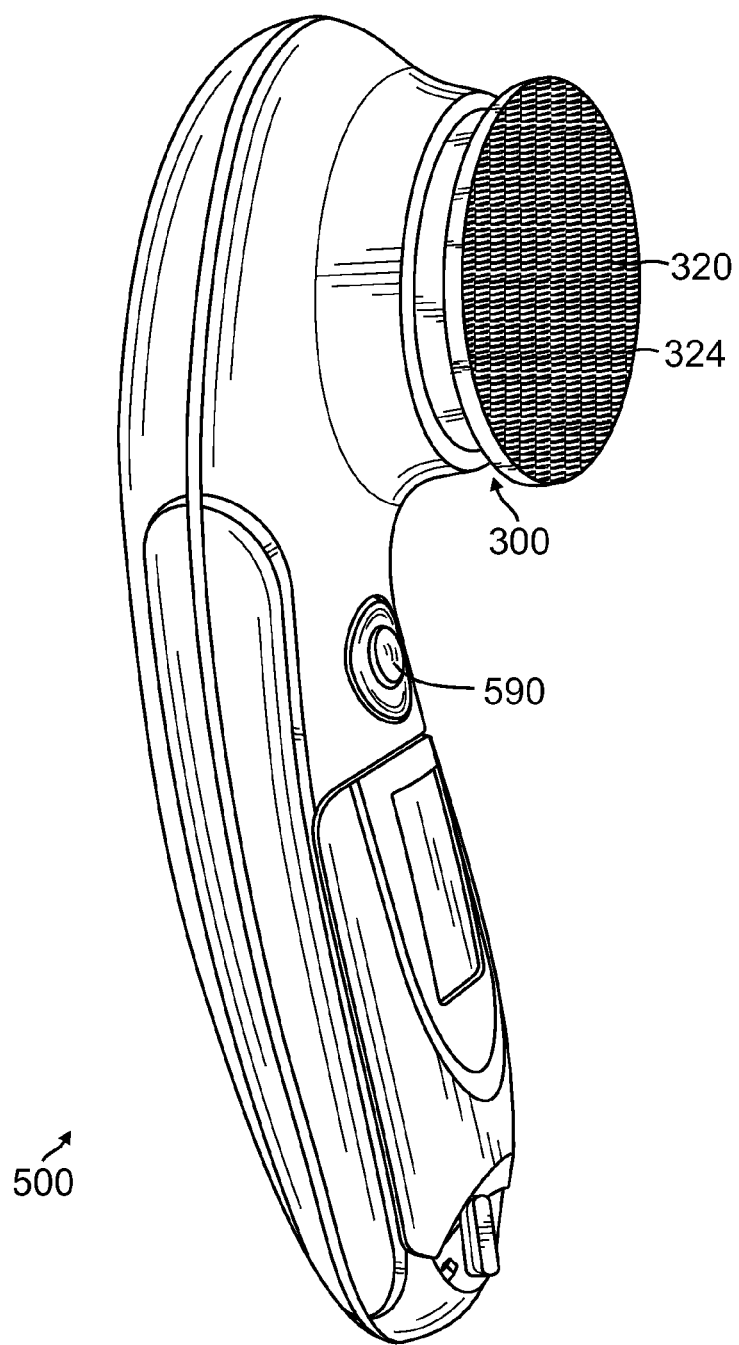
FIG. 2B is a perspective view of the motorized hand piece and mechanical rotatable coupling shaft with the interface cup member affixed so that the hook and loop fasteners are exposed to receive the different exfoliating members.

Referring to FIGS. 2, 2A and 2B, the innovation of the present invention is that the hand-piece 500 can retain a multiplicity of different interchangeable components which are used for different purposes and which comprises an interface cup member 300 which includes a body 312 with a sidewall 310 (see FIG. 2A) separating an upper or first surface 320 retaining an affixation means 322 including hook and loop fastener 324 (see FIG. 2B) which will retain a corresponding hook and loop fastener member from the base of a cleansing apparatus to be described. The body 312 also includes a lower or second surface 330 having interface cup member retaining opening 332 located at the center of the second surface 330. The cup retaining opening 332 is affixed onto the coupling member 588 of mechanical rotatable coupling shaft 580. When the motor 550 is turned on, the interface retaining cup member 300 along with the hook and loop fastener 324 is caused to rotate. Any object having a lower surface with a corresponding hook and loop fastener 324 is removably affixed to the hook and loop fastener 324 of the interface retaining cup member 300 and will rotate with it. FIG. 2B discloses the interface cup 300 affixed to the coupling shaft 588 of the motorized hand-piece 500 with the surface containing the hook and loop fastener 324 exposed to receive a base member having a mating hook and loop fastener on one surface and an embedded exfoliating member on its opposite surface.

Figure 3:
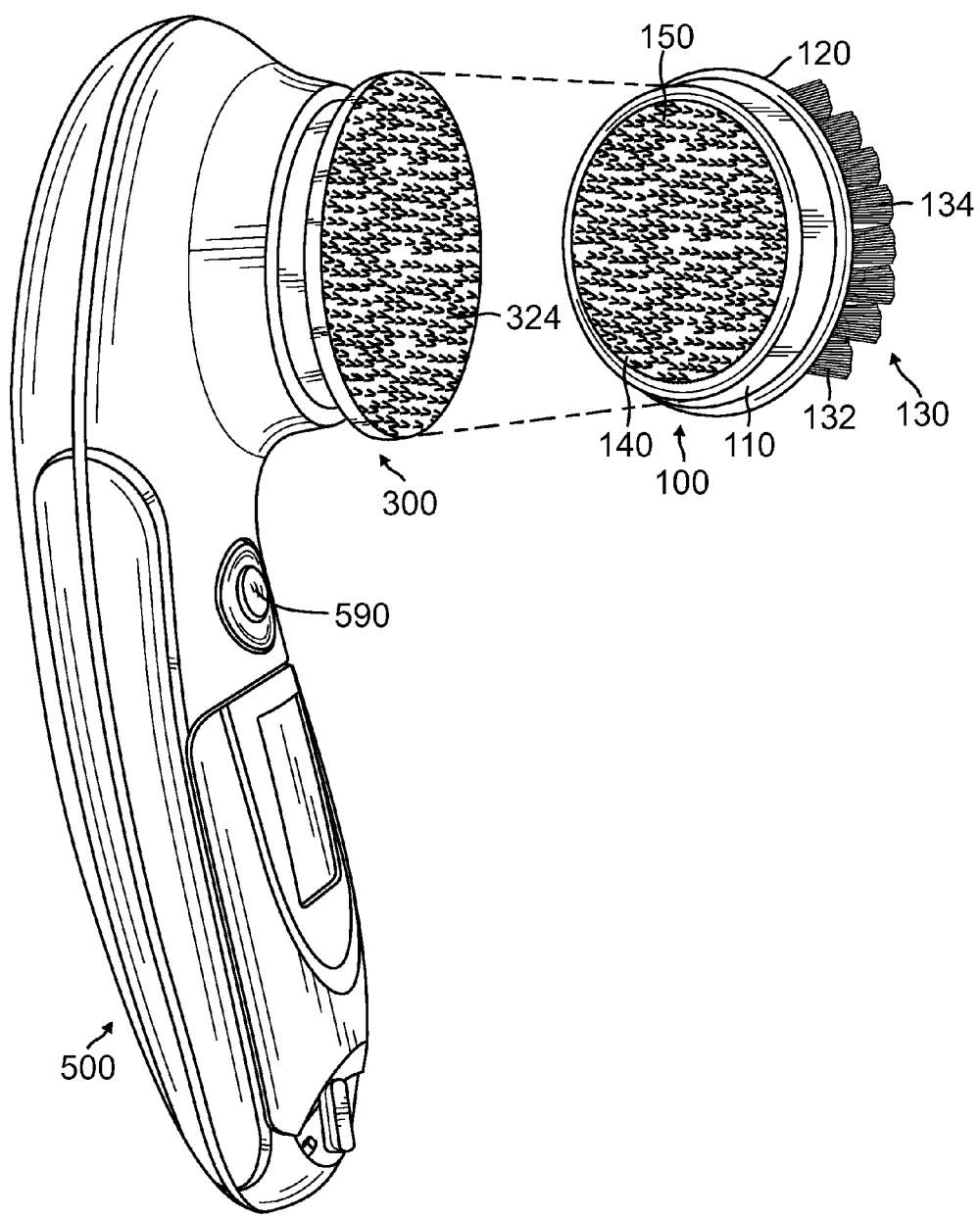
FIG. 3 is a perspective view of the handheld motorized piece with the interface cup member attached on the left side and a rear perspective view of the exfoliating brush base member showing the rear surface having a multiplicity of mating hook and loop fasteners to mate with the hook and loop fasteners on the interface cup member with the bristles also shown on the opposite side.
Figure 3A:
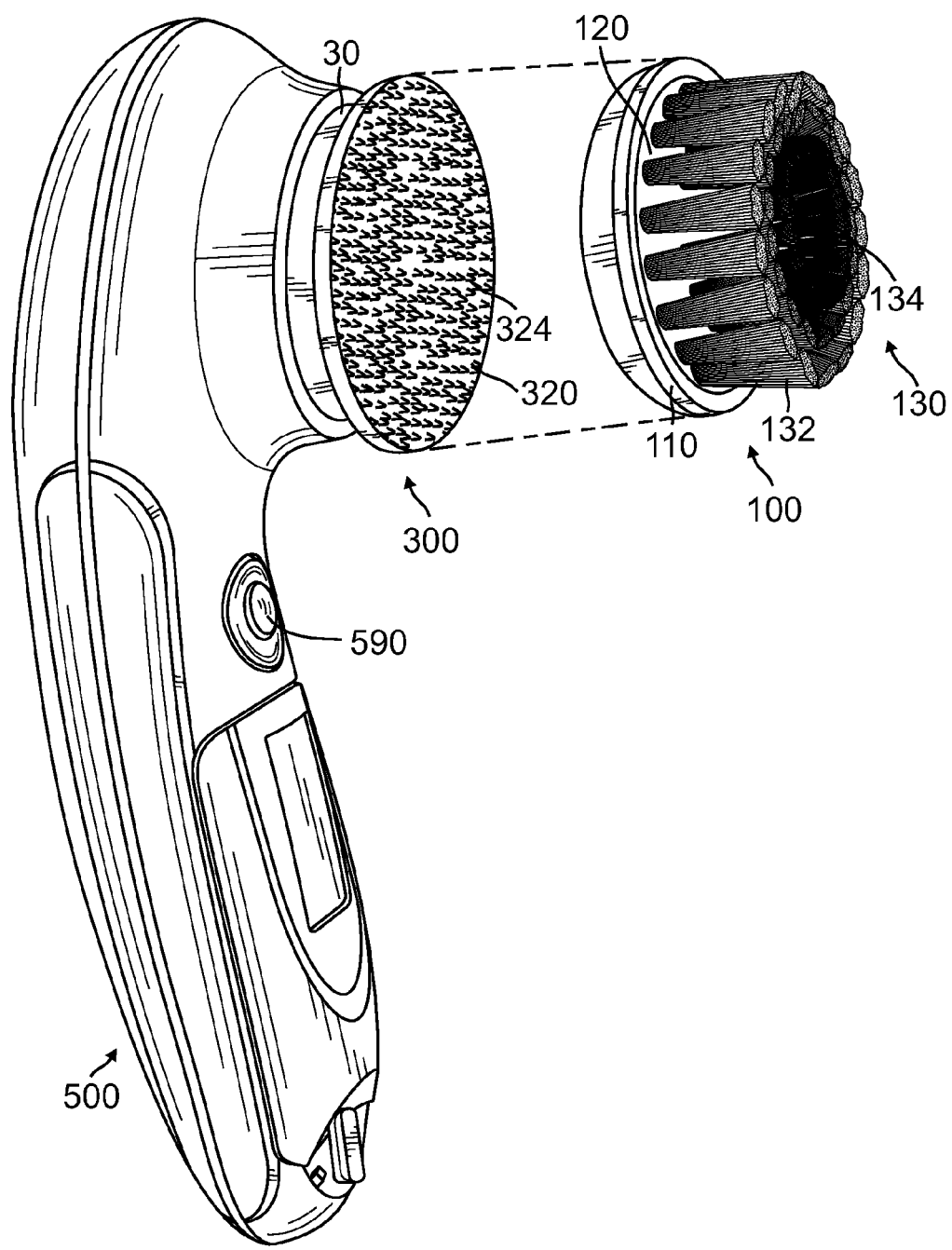
FIG. 3A is a perspective view of the handheld motorized piece with the interface cup member attached on the right side with the attachable member with the bristles shown embedded on the top surface of the microdermabrasion brush base member.
Figure 3B:
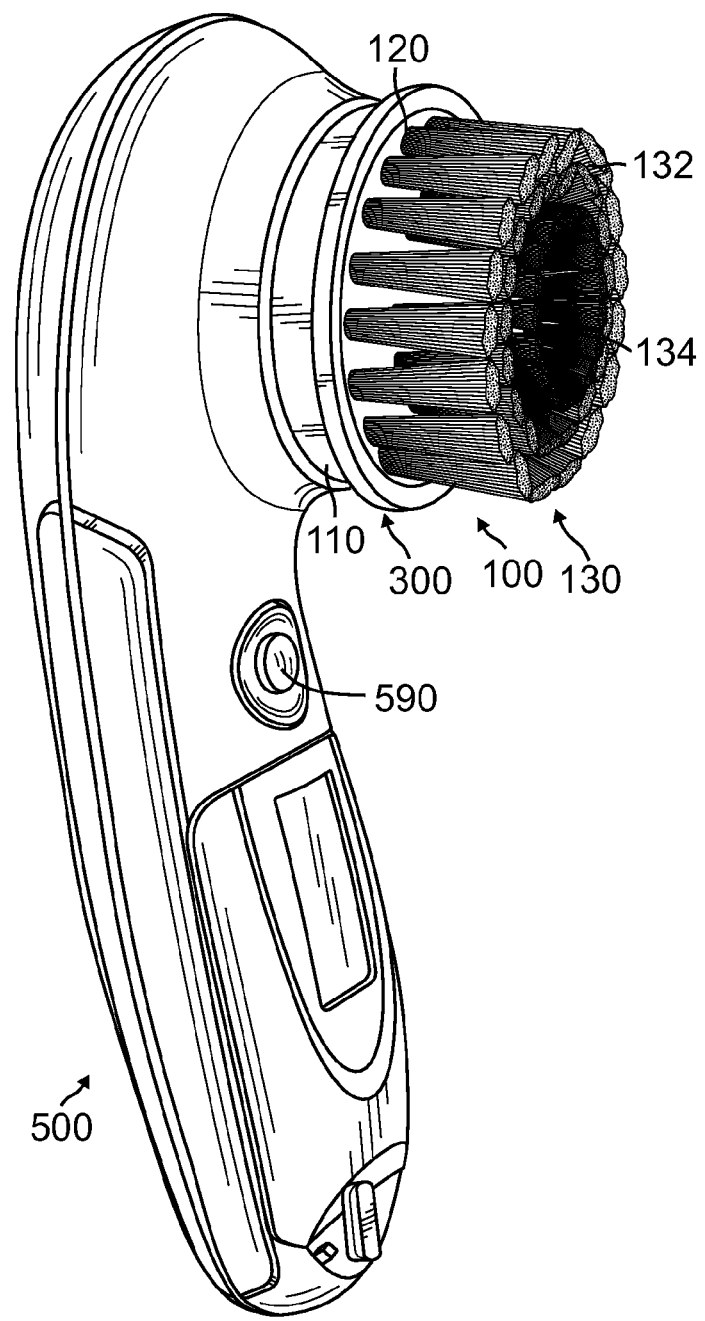
FIG. 3B is a perspective view showing the microdermabrasion brush member retained onto the handheld motorized piece with the hook and loop fasteners of the microdermabrasion brush mating with the hook and loop fasteners from the interface cup member.

Referring to FIGS. 3, 3A, and 3B, one accessory used with the present invention is microdermabrasion brush assembly 100 with the interface cup 300 affixed to the coupling member 588 of the motorized hand-piece 500 with the surface containing the hook and loop fastener 324 exposed to receive a base member 100 having a sidewall 110 with a lower surface 140 having mating hook and loop fasteners 150 on the lower surface which mate with the hook and loop fasteners 324 and a flat upper surface 120 into which a multiplicity of exfoliating microdermabrasion brush bristles 130 are affixed. The microdermabrasion brush bristles 130 may have an outer ring of fine bristles 132 and an interior ring of coarse bristles 134. The rear view of the microdermabrasion brush base member is illustrated in FIG. 3 and the front view of the microdermabrasion brush base member 100 is illustrated in FIG. 3A.

Referring to FIG. 3B, the microdermabrasion brush base member 100 is removably affixed to the motorized hand-piece 500 with the mating hook and loop fasteners 150 affixed to the hook and loop fasteners 324. When the motor 550 is turned on, the microdermabrasion brush assembly 100 rotates so that the microdermabrasion bristles 132 and 134 exfoliate the top layer of facial skin as the hand piece 500 is held so that the microdermabrasion bristles 132 and 134 are against facial skin.

Figure 4:
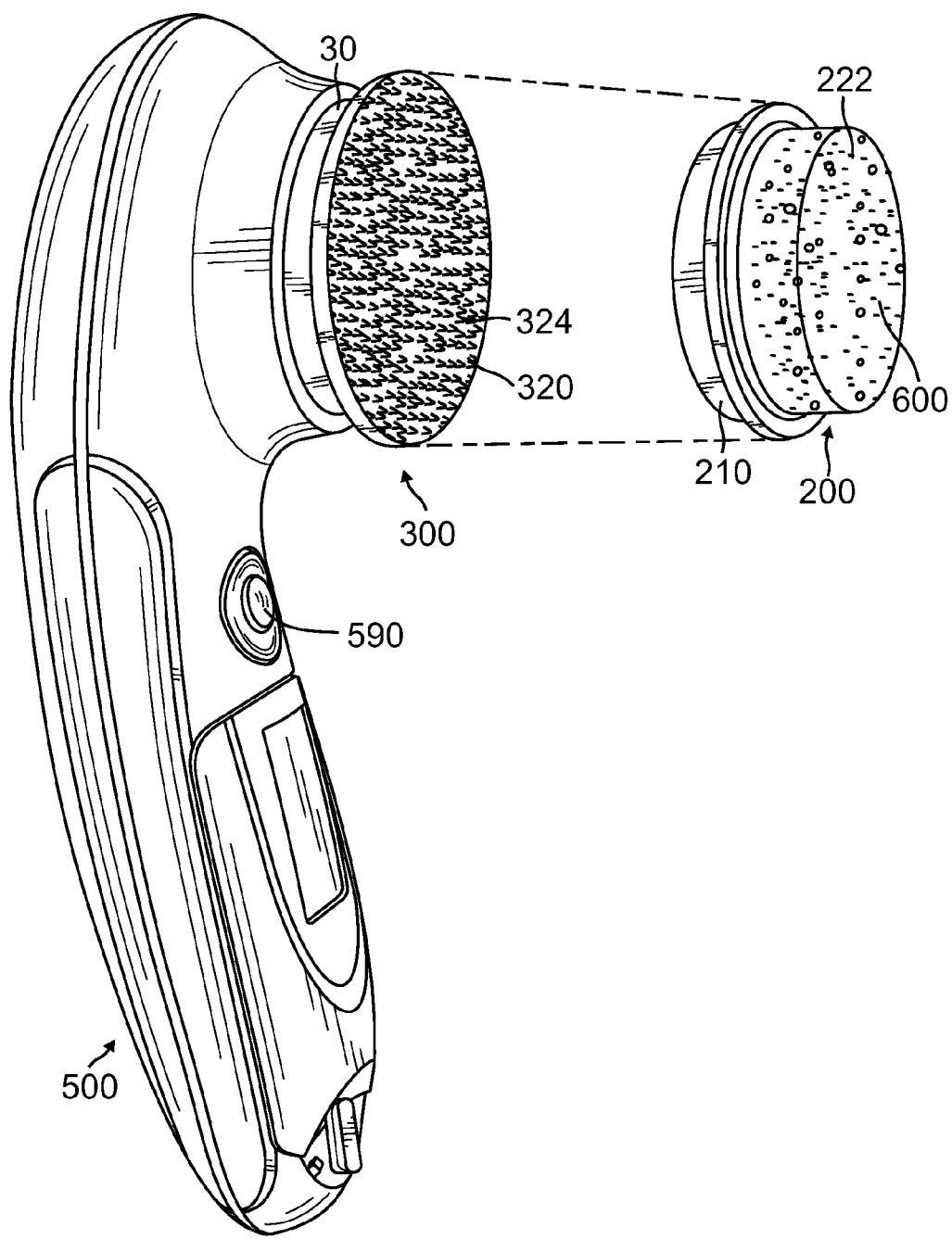
FIG. 4 is a is a perspective view of the handheld motorized piece with the interface cup member attached on the left side and a front perspective view showing the base sponge retaining base assembly showing the front removable latex sponge and makeup applied thereto.
Figure 4A:
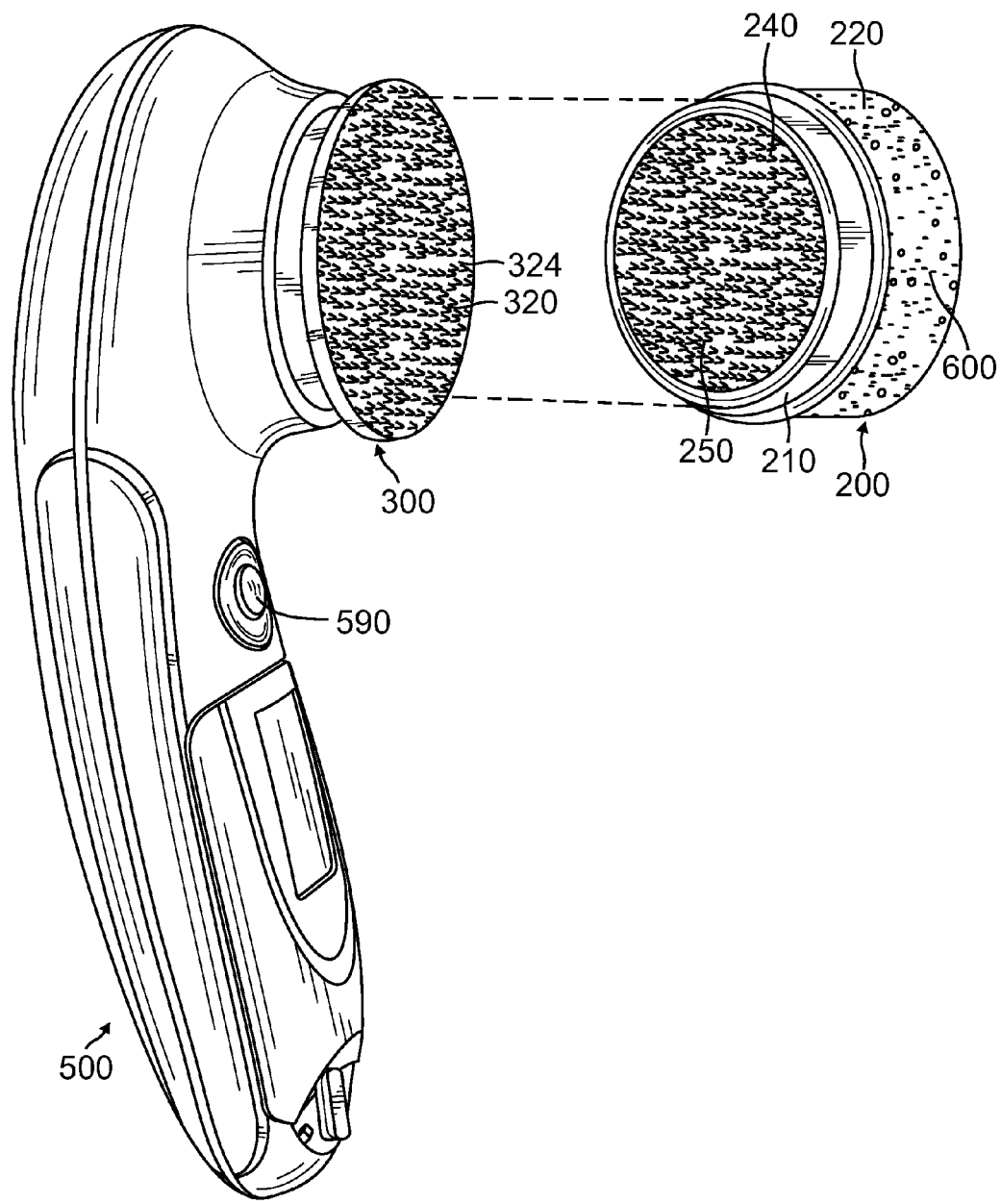
FIG. 4A is a perspective view of the handheld motorized piece with the interface cup member attached on the left side and a rear perspective view of the base sponge retaining base assembly showing the mating hook and loop fasteners which will mate with the hook and loop fasteners on the interface cup member.
Figure 4B:
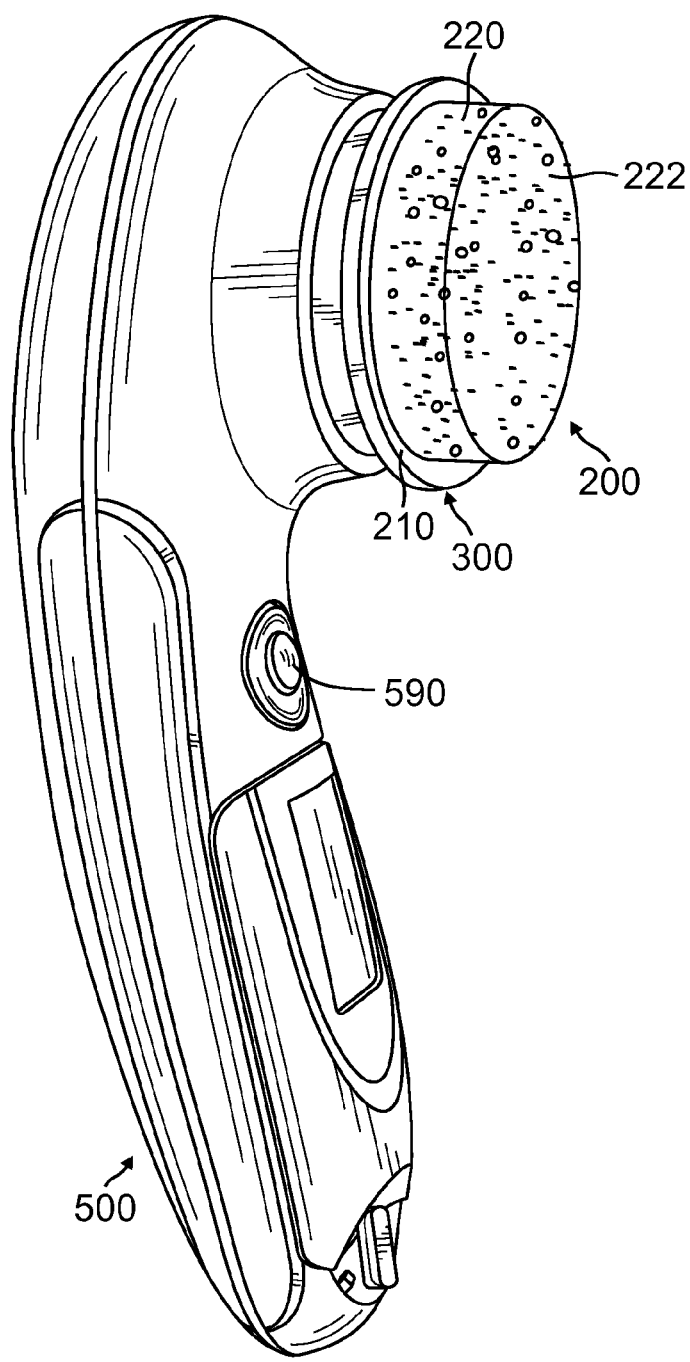
FIG. 4B is a perspective view the base sponge retaining base member retained onto the handheld motorized piece with the hook and loop fasteners of the base sponge retaining base assembly with latex sponge mating with the hook and loop fasteners of the interface cup member.

Referring to FIGS. 4, 4A and 4B, a second accessory used with the present invention is a latex sponge retained in a base sponge retaining base assembly 200. On the left side of the exploded views in FIG. 4 and FIG. 4A, there is once again illustrated the interface cup 300 affixed to the coupling member 588 of the motorized hand-piece 500 with the surface containing the hook and loop fastener 324 exposed to receive a base member having a mating hook and loop fastener on one surface and an embedded exfoliating member on its opposite surface. In the exploded views of FIGS. 4 and 4A, the latex sponge assembly is illustrated removed from the interface cup 300 and its hook an loop fastener 324. FIG. 4B is a perspective view of the motorized hand piece 500 with the latex sponge assembly retained onto the interface cup by respective hook and loop fasteners 324 and 250.

The latex sponge base assembly 200 includes a retaining member 210 retaining the latex sponge 220 having an upper surface 222 which is used to apply moisturizer and makeup 600 to skin when the moisturizer and/or makeup is placed onto the upper surface 222 of the latex sponge.

Referring to FIG. 4A, the bottom surface 240 of the retaining member 210 of the latex sponge assembly 220 is illustrated. A mating hook and loop fastener member 250 is affixed to the bottom surface 240. The mating hook and loop faster member 250 is configured to be retained by hook and loop fastener member 324.

Referring to FIG. 4B, the latex base sponge assembly 200 is removably affixed to the motorized hand-piece 500 with the mating hook and loop fasteners 250 affixed to the hook and loop fasteners 324. When the motor is turned on, the latex sponge assembly 200 rotates so that the latex sponge 220 applies moisturizer and/or makeup to facial skin as the hand-piece 500 is held so that the upper surface 222 of the latex sponge 220 is against the skin.

Figure 5:
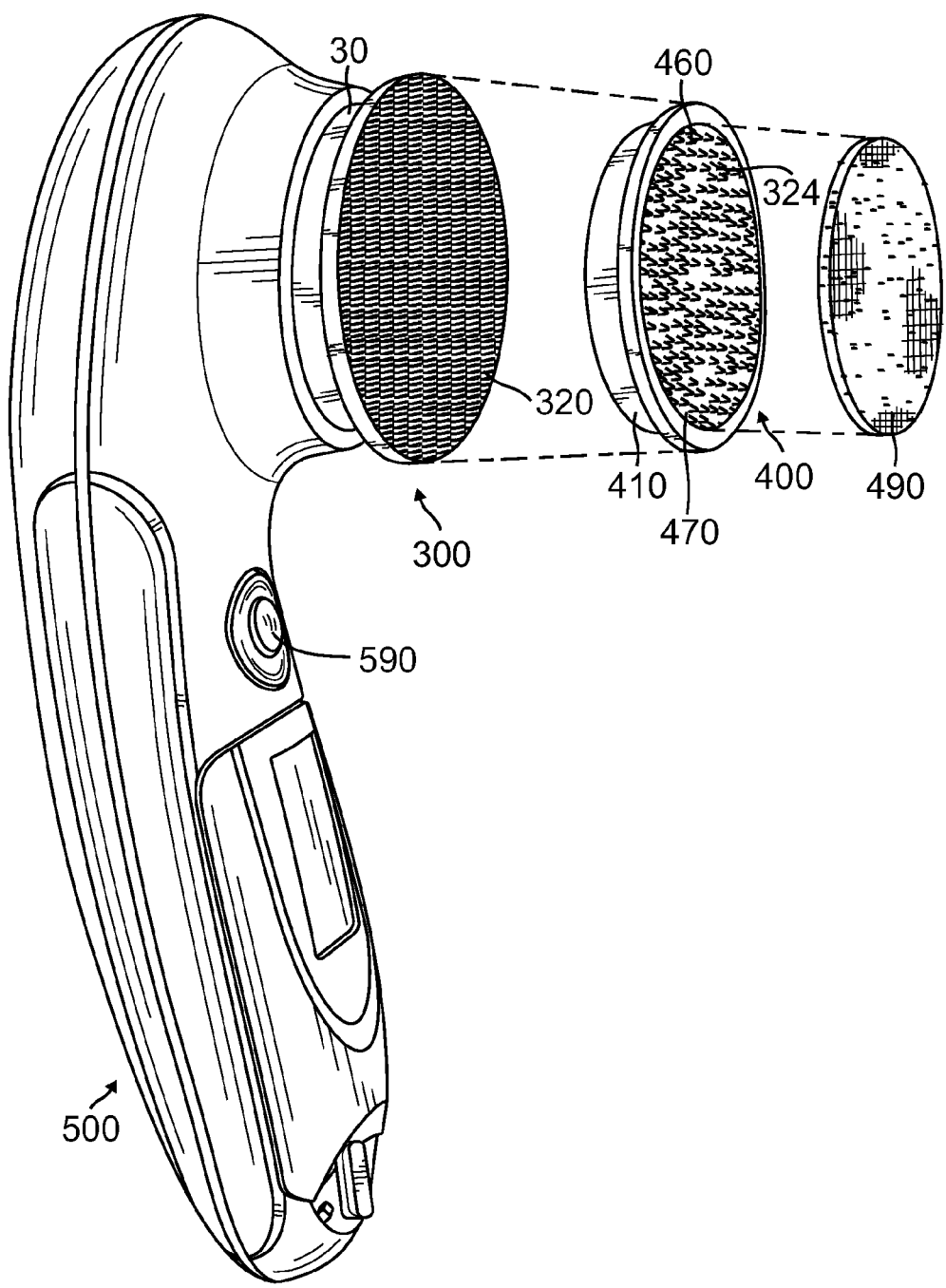
FIG. 5 is a is a perspective view of the handheld motorized piece with the interface cup member attached on the left side and a front perspective view showing the base deep cleaning pad retainer with hook and loop fasteners on the front surface and a deep cleaning pad removed therefrom.
Figure 5A:
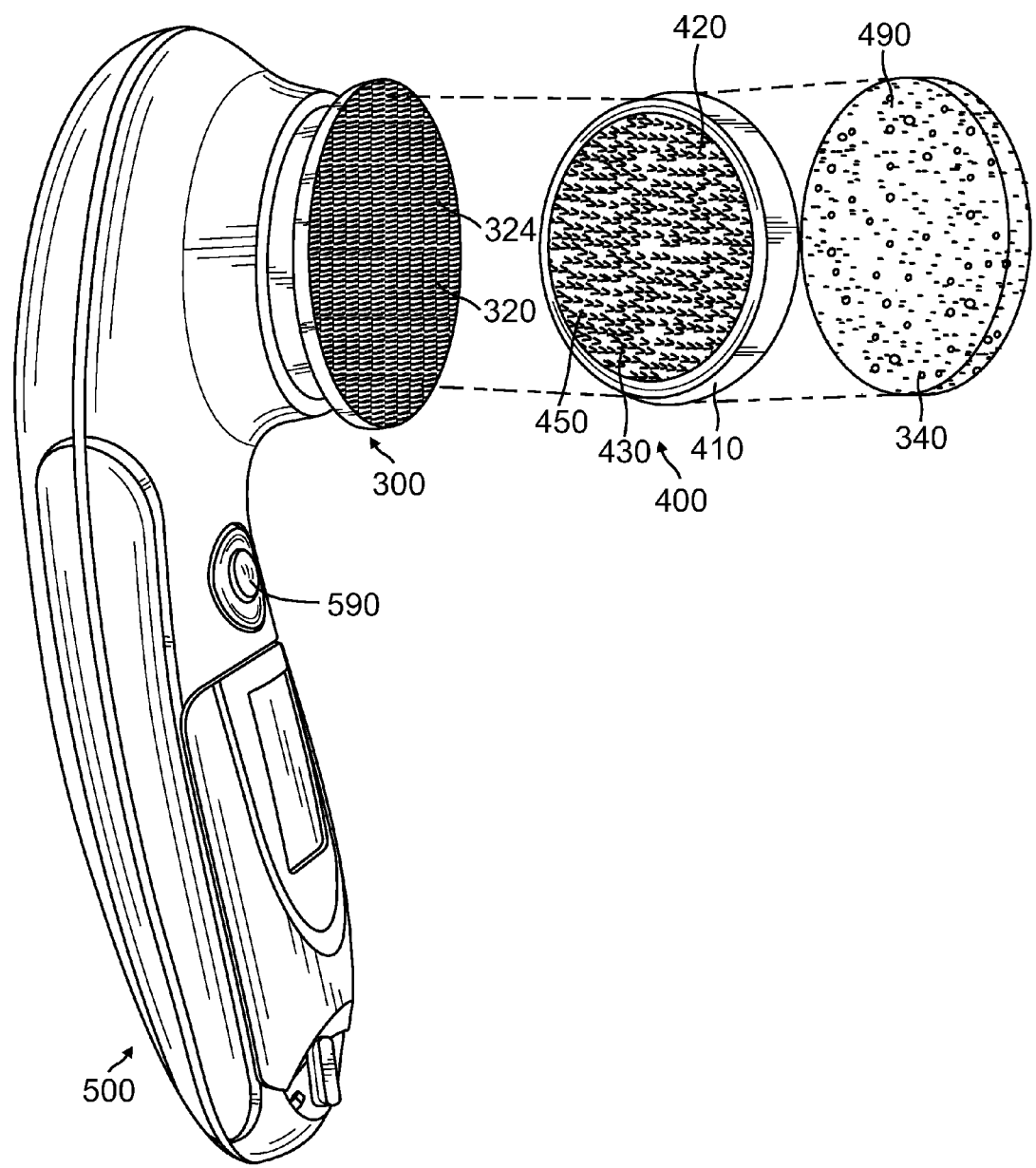
FIG. 5A is a perspective view of the handheld motorized piece with the interface cup member attached on the left side and a rear perspective view of the base deep cleaning pad retainer showing the mating hook and loop fasteners which will mate with the hook and loop fasteners on the interface cup member, and a deep cleaning pad removed therefrom.
Figure 5B:
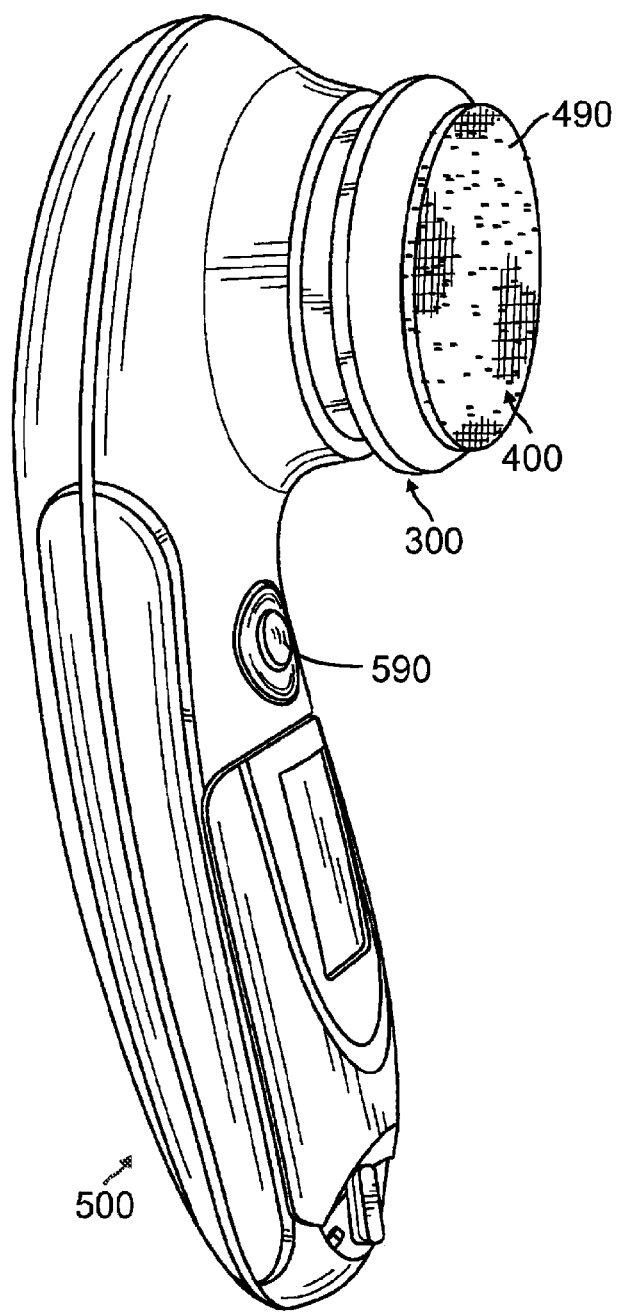
FIG. 5B is a perspective view the handheld motorized piece with the interface cup member attached and the base deep cleaning pad retainer retained onto the handheld motorized piece with the hook and loop fasteners on the bottom surface of the base deep cleaning pad retainer affixed to the hook and loop fasteners of the interface cup, and in turn the deep cleaning pad affixed by the hook and loop fasteners on the front surface of the base deep cleaning pad retainer.

Referring to FIGS. 5A, 5B and 5C, a third accessory used with the present invention is a hook and loop fastening member assembly 400 is illustrated. In FIG. 5 there is a perspective exploded view with the motorized hand piece and interface cup on the left and a deep cleaning sponge retainer on the right. On the left side of the exploded views in FIG. 5 and FIG. 5A, there is once again illustrated the interface cup 300 affixed to the coupling member 588 of the motorized hand-piece 500 with the surface containing the hook and loop fastener 324 exposed to receive a base member having a mating hook and loop fastener on one surface and another mating hook and loop fastener on the other side embedded on its opposite surface. In the exploded views of FIGS. 5 and 5A, there is illustrated a hook and loop fastening deep cleaning pad base member assembly 400 which includes a retaining cup 410.

Referring to FIG. 5, the hook and loop deep cleaning pad base assembly 400 includes a retaining cup 410, and hook and loop fasteners 460 retained on exterior surface 470 of the retaining cup 410, and a deep cleansing pad 490 is removably affixed to the hook and loop fasteners 460. As illustrated in FIG. 5A, the bottom surface 420 of retaining cup 410 has mating hook and loop fasteners 450 designed to mate with and be retained by hook and loop fasteners 324.

Referring to FIG. 5B, the bottom surface the mating hook and loop fasteners 324 and 450 are engaged to retain the deep cleaning pad retainer 400 to the motorized hand-piece 500 with the deep cleaning pad 490 retained by hook and lop fasteners 460. When the motor 550 is turned on, the deep cleaning pad retainer assembly 400 rotates so that the affixed deep cleaning or cleansing pad 469 also rotates so that the cleansing or cleansing pad 490 is held against the skin by holding the hand-piece 500 so that the deep cleaning or cleansing pad 490 is against facial skin. When the deep cleaning or cleansing pad 490 is used up, it is simply removed from the hook and loop fasteners 460 and replaced with a new deep cleaning or cleansing pad 490.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A handheld motorized hand-piece having a mechanical rotatable coupling shaft with a coupling member at its distal end, comprising:

a. an interface cup member which is a separate component from the handheld motorized hand piece, the interface cup member including a body with a sidewall separating a first surface retaining a hook or loop fastener from a second surface of the body including a retaining opening at a center of the second surface, the retaining opening removably affixed onto the coupling member of the coupling shaft so that the interface cup is rotatably affixed to the coupling member and the first surface of the interface cup faces away from the handheld motorized hand-piece;

b. a combination selected from the group consisting of a first base member having a microdermabrasion brush embedded in an exterior surface with a retaining member on an interior surface, a second base member having an exterior surface with a latex sponge retainer to retain a latex sponge for moisturizing cream and makeup application and a retaining member on an interior surface, and a third base member having a hook and loop fastening member on an exterior surface which removably retains a disposable cleansing pad, and a retaining member on an interior surface;

c. the retaining member on the interior surface of the first base member including a mating hook or loop fastener by which the retaining member is affixed onto the hook or loop fastener of the first surface of the interface cup;

d. the retaining member of the interior surface of the second base member including a mating hook and or loop fastener by which the retaining member is affixed onto the hook and or loop fastener of the first surface of the interface cup;

e. the retaining member of the third base member including a mating hook or fastener by which the retaining member is affixed onto the hook or loop fastener of the first surface of the interface cup;

f. the respective base members having the microdermabrasion brush, the latex sponge retainer, the hook and loop fastening member retaining the disposable cleansing pad which is replaced with a new cleansing pad when the disposable cleansing pad is used up, the respective base members are each interchangeably retained onto the hook and or loop fastener of the interface cup; and when a motor of the motorized hand-piece hand piece is turned on, the interface cup is caused to rotate and a respective base member affixed to the interface cup also rotates.

2. A handheld apparatus comprising:

a. a motorized hand-piece which includes an outer shell which surrounds an interior chamber, the interior chamber includes a power source member electrically connected to a motor which in turn is connected to a shaft with at least one gear at a distal end of the shaft remote from a proximal end of the shaft connected to the motor, the hand-piece exterior shell including a raised section having a flat upper surface base surrounding an opening through which a mechanical rotatable coupling shaft extends through its distal end, at its proximal end within the interior chamber, a proximal end of the mechanical rotatable coupling shaft has at least one gear which is intermeshed with the at least one gear of the motor so that as the motor gear rotates when the motor is energized, the mechanical rotatable coupling shaft is caused to rotate so that it imparts a rotating motion which is parallel to the upper surface of the hand piece and to an object affixed to a coupling member at the distal end of the mechanical rotatable coupling shaft, the hand-piece also includes an on/off switch, when pressed, the on/off switch closes an electric circuit connecting the motor to the source of power and an intermesh movement of the respective at least one gears causes rotational motion of the mechanical rotatable coupling shaft;

b. an interface cup member which is a separate component to the handheld motorized hand-piece, the interface cup member including a body, a sidewall separating a first surface retaining a hook or loop fastener from a second surface of the body including a retaining opening at a center of the second surface, the retaining opening removably affixed onto the coupling member of the coupling shaft so that the interference cup is rotatably affixed to the coupling member and the first surface of the interface cup faces away from the handheld motorized hand-piece; the hook or loop fastener on the first surface of the interface cup individually retaining a multiplicity of different interchangeable components which are used for different purposes;

d. one interchangeable component identified in part c of the claim is a microdermabrasion brush assembly having a retaining cup with a flat upper surface into which a multiplicity of exfoliating microdermabrasion brush bristles are affixed, the microdermabrasion brush bristles having an outer ring of fine bristles and an interior ring of coarse bristles, a bottom surface of the retaining cup including a mating hook or loop fastener affixed to the hook or loop fastener of the first surface of the interface cup and when the motor is turned on, the microdermabrasion brush assembly rotates so that the microdermabrasion brushes exfoliate the top layer of facial skin as the hand piece is held so that the microdermabrasion bristles are against facial skin;

e. a second interchangeable component identified in part c of the claim is a retaining cup with an exterior surface retaining a latex sponge having an upper surface which is used to apply moisturizer or makeup to skin when the moisturizer or makeup are placed on the upper surface of the latex sponge, the retaining cup with an exterior bottom surface having mating hook or loop fasteners which mate with the hook or loop fasteners of the first surface of the interface cup and when the motor is turned on, the latex sponge assembly rotates so that the moisturizer and make-up cream is applied to facial skin as the hand piece is held so that the latex sponge is against the facial skin; and f. a third interchangeable component identified in part c of the claim is a retaining cup with an exterior surface retaining hook and loop fasteners which removably retains a disposable cleansing pad, a bottom surface of the retaining cup including a mating hook or loop fastener affixed to the hook or loop fastener of the interface cup and when the motor is turned on, the disposable cleansing pad rotates so that the disposable cleansing pad cleans facial skin as the hand piece is held so that the disposable cleansing pad is against the skin, and when the disposable cleansing pad is used up, the disposable cleansing pad is removed from the exterior surface retaining hook and loop fasteners and replaced with a new disposable cleansing pad.

3. The apparatus in accordance with claim 2, further comprising: the power source in the hand piece is batteries.

4. The apparatus in accordance with claim 2, further comprising the power source in the hand-piece is 120-volt electricity.

5. A handheld apparatus comprising:

a. a motorized hand-piece including a mechanical rotatable coupling shaft which is caused to rotate so that it imparts a rotating motion to a coupling member at a distal end of the coupling shaft;

b. an interface cup member which is a separate component to the handheld motorized hand-piece the interface cup member including a body, a sidewall separating a first surface retaining a hook or loop fastener from a second surface of the body including a retaining opening at a center of the second surface, the retaining opening removably affixed onto the coupling member of the coupling shaft so that the interface cup is rotatably affixed to the coupling member and the first surface of the interface cup faces away from the handheld motorized handpiece; and the hook or loop fastener on the first surface of the interface cup individually retaining a multiplicity of different interchangeable retaining cups which are used for different purposes, each different retaining cup including a bottom surface including a mating hook or loop fastener affixed to the hook or loop fastener of the interface cup and which rotate when the motorized hand piece is energized and causes the interface cup to rotate.

6. The handheld apparatus in accordance with claim 5, further comprising: an interchangeable retaining cup of the multiplicity of retaining cups includes a microdermabrasion brush assembly, wherein the interchangeable retaining cup includes a flat upper surface into which a multiplicity of exfoliating microdermabrasion brush bristles are affixed.

7. The handheld apparatus in accordance with claim 6, further comprising: the microdermabrasion brush bristles have an outer ring of fine bristles and a inner ring of coarse bristles.

8. The handheld apparatus in accordance with claim 5, further comprising: an interchangeable retaining cup of the multiplicity of retaining cups, wherein the interchangeable retaining cup is a latex sponge assembly which includes a retaining member retaining the latex sponge having an upper surface which is used to apply moisturizer and makeup to skin when the moisturizer or makeup are placed on the upper surface of the latex sponge.

9. The handheld apparatus in accordance with claim 5, further comprising: an interchangeable retaining cup of the multiplicity of retaining cups, wherein the interchangeable retaining cup is a hook and loop fastening member assembly which includes an exterior surface retaining hook and loop fasteners which removably retain a disposable cleansing pad, and when the disposable cleaning pad is used up, the disposable cleansing pad is removed from the hook and loop fastening member assembly and replaced with a new disposable cleaning pad.

* * * * *